(12) United States Patent
Herfert et al.

(10) Patent No.: US 8,703,876 B2
(45) Date of Patent: Apr. 22, 2014

(54) PROCESS FOR PRODUCING WATER ABSORBING POLYMER PARTICLES WITH IMPROVED COLOR STABILITY

(75) Inventors: Norbert Herfert, Altenstadt (DE); Thomas Daniel, Waldsee (DE); Bootsara Parchana, Chonburi (TH)

(73) Assignee: BASF SE, Ludwigshafen (DE)

( * ) Notice: Subject to any disclaimer, the term of this patent is extended or adjusted under 35 U.S.C. 154(b) by 175 days.

(21) Appl. No.: 13/041,033

(22) Filed: Mar. 4, 2011

(65) Prior Publication Data

US 2011/0224381 A1    Sep. 15, 2011

Related U.S. Application Data

(60) Provisional application No. 61/313,817, filed on Mar. 15, 2010.

(30) Foreign Application Priority Data

Mar. 15, 2010  (EP) ..................................... 10156480

(51) Int. Cl.
 *C08F 8/40* (2006.01)
 *C08F 4/40* (2006.01)
 *C08F 20/18* (2006.01)

(52) U.S. Cl.
 USPC ........ 525/329.8; 525/340; 524/831; 524/832; 524/133; 524/284; 604/372; 604/358

(58) Field of Classification Search
 USPC ............... 525/329.8, 340; 524/831, 832, 133, 524/284; 604/372, 358
 See application file for complete search history.

(56) References Cited

U.S. PATENT DOCUMENTS

| 5,185,413 | A  | * | 2/1993  | Yoshinaga et al. ............. 526/233 |
| 6,359,049 | B1 | * | 3/2002  | Carrico et al. ................. 524/414 |
| 7,179,875 | B2 |   | 2/2007  | Fuchs et al. |
| 7,504,551 | B2 | * | 3/2009  | Herfert et al. ................. 604/372 |
| 7,714,061 | B2 |   | 5/2010  | Riegel et al. |
| 7,816,426 | B2 | * | 10/2010 | Ahmed et al. ................. 523/200 |
| 2010/0041550 | A1 |   | 2/2010 | Riegel et al. |
| 2010/0286287 | A1 |   | 11/2010 | Walden |
| 2011/0042612 | A1 |   | 2/2011 | Riegel et al. |

FOREIGN PATENT DOCUMENTS

| JP | 05086251 A   | * | 4/1993  |
| WO | WO-00/55245 A1  |   | 9/2000  |
| WO | WO-03/014172 A2 |   | 2/2003  |
| WO | WO-2004/084962 A1 |   | 10/2004 |
| WO | WO 2004084962 A1 | * | 10/2004 |
| WO | WO 2005012369 A1 | * | 2/2005 |
| WO | WO-2006/058682 A1 |   | 6/2006 |
| WO | WO-2008/092842 A1 |   | 8/2008 |
| WO | WO-2008/092843 A1 |   | 8/2008 |
| WO | WO-2009/060062 A1 |   | 5/2009 |

OTHER PUBLICATIONS

WO 2005012369 A1, Feb. 2005, Machine translation.*
JP 05-086251, Apr. 1993, Shimada et al., Machine translation.*
Buchholz et al. (eds.), Modern Superabsorbent Polymer Technology, Wiley-VCH, pp. 71-103 (1998).

* cited by examiner

*Primary Examiner* — Satya Sastri
(74) *Attorney, Agent, or Firm* — Marshall, Gerstein & Borun LLP

(57) ABSTRACT

A process for producing water-absorbing polymer particles, wherein at least one inorganic phosphoric acid and/or salt thereof and at least one organic 2-hydroxy acid and/or salt thereof is added, where the phosphorus in the inorganic phosphoric acid has an oxidation number of less than +V and the organic 2-hydroxy acid does not have any ethylenically unsaturated groups, and also the water-absorbing polymer particles obtainable by the process according to the invention.

12 Claims, No Drawings

PROCESS FOR PRODUCING WATER ABSORBING POLYMER PARTICLES WITH IMPROVED COLOR STABILITY

CROSS-REFERENCE TO RELATED APPLICATIONS

This application claims the benefit of U.S. provisional patent application 61/313,817, filed Mar. 15, 2010, incorporated herein by reference in its entirety.

The present invention relates to processes for producing water-absorbing polymer particles, wherein at least one inorganic phosphoric acid and/or salt thereof and at least one organic 2-hydroxy acid and/or salt thereof is added, where the phosphorus in the inorganic phosphoric acid has an oxidation number of less than +V and the organic 2-hydroxy acid does not have any ethylenically unsaturated groups, and to the water-absorbing polymer particles obtainable by the process according to the invention.

Water-absorbing polymer particles are used to produce diapers, tampons, sanitary napkins and other hygiene articles, but also as water-retaining agents in market gardening. The water-absorbing polymer particles are also referred to as superabsorbents.

The production of water-absorbing polymer particles is described in the monograph "Modern Superabsorbent Polymer Technology", F. L. Buchholz and A. T. Graham, Wiley-VCH, 1998, pages 71 to 103.

The properties of the water-absorbing polymer particles can be adjusted, for example, via the amount of crosslinker used. With increasing amount of crosslinker, the centrifuge retention capacity (CRC) falls and the absorption under a pressure of 21.0 g/cm$^2$ (AUL0.3 psi) passes through a maximum.

To improve the application properties, for example permeability of the swollen gel bed (SFC) in the diaper and absorption under a pressure of 49.2 g/cm$^2$ (AUL0.7 psi), water-absorbing polymer particles are generally surface postcrosslinked. This increases the degree of crosslinking of the particle surface, which allows the absorption under a pressure of 49.2 g/cm$^2$ (AUL0.7 psi) and the centrifuge retention capacity (CRC) to be at least partly de-coupled. This surface postcrosslinking can be performed in the aqueous gel phase. Preferably, however, dried, ground and screened-off polymer particles (base polymer) are surface coated with a surface postcrosslinker, thermally surface postcrosslinked and dried. Crosslinkers suitable for this purpose are compounds which can form covalent bonds with at least two carboxylate groups of the water-absorbing polymer particles.

A problem which often occurs in water-absorbing polymer particles is that of discoloration, which occurs in the course of storage at elevated temperature or elevated air humidity. Such conditions often occur in the course of storage in tropical or subtropical countries. Under such conditions, water-absorbing polymer particles tend to yellow; they may even take on a brown or even almost black color. This discoloration of the actually colorless water-absorbing polymer particles is unsightly and undesired, since it is visible especially in the desired thin hygiene products, and consumers reject unsightly hygiene products. The cause of the discoloration has not been entirely clarified, but reactive compounds such as residual monomers from the polymerization, the use of some initiators, impurities in the monomers or in the neutralizing agent, surface postcrosslinkers or stabilizers in the monomers used appear to play a role.

According to WO 00/55245 A1, the color stability of water-absorbing polymer particles can be improved by adding inorganic reducing agents. The inorganic reducing agents can be added, for example, to the polymer gel after the polymerization, or after the thermal surface postcrosslinking.

WO 2006/058682 A1 teaches that the presence of oxygen in the thermal surface postcrosslinking leads to discoloration.

According to WO 2004/084962 A1, the use of sulfinic acids as polymerization initiators has a favorable effect on the color stability of the water-absorbing polymer particles obtained.

WO 2008/092842 A1 and WO 2008/092843 A1 disclose coating with basic salts for the same purpose.

According to WO 2009/060062 A1, the color stability of water-absorbing polymer particles with sulfonic acids and salts thereof can be increased, in which case the sulfonic acids or salts thereof are preferably added directly before the surface postcrosslinking.

WO 03/014172 A2 describes a process for producing water-absorbing polymer particles, wherein the acrylic acid used has been treated beforehand with an aldehyde scavenger, since the presence of aldehydes in particular is said to lead to discoloration.

It was an object of the present invention to provide a process for producing water-absorbing polymer particles with improved color stability. At the same time, the water-absorbing polymer particles, especially in the course of prolonged storage in a warm and moist environment, should not develop any unpleasant odors.

The object is achieved by a process for producing water-absorbing polymer particles by polymerizing a monomer solution or suspension comprising
  a) at least one ethylenically unsaturated monomer which bears acid groups and may be at least partly neutralized,
  b) at least one crosslinker,
  c) at least one initiator,
  d) optionally one or more ethylenically unsaturated monomers copolymerizable with the monomers mentioned under a) and
  e) optionally one or more water-soluble polymers,
comprising the steps of polymerizing the monomer solution to give a polymer gel i), optionally comminuting the resulting polymer gel ii), drying the polymer gel iii), grinding and classifying the dried polymer gel to polymer particles iv), and optionally thermally surface postcrosslinking the classified polymer particles v), which comprises adding, before, during or after one of steps i) to v), separately or together,
  at least one inorganic phosphoric acid and/or salt thereof and
  at least one organic 2-hydroxy acid and/or salt thereof,
where the phosphorus in the inorganic phosphoric acid has an oxidation number of less than +V and the organic 2-hydroxy acid does not have any ethylenically unsaturated groups.

The inorganic phosphoric acids and/or salts thereof and the organic 2-hydroxy acids and/or salts thereof are preferably metered in in the form of aqueous solutions.

Suitable inorganic phosphoric acids and/or salts thereof are hypophosphorous acid, hypophosphorous acid, ammonium phosphite, ammonium hypophosphite, sodium phosphite, sodium hypophosphite, potassium phosphite and potassium hypophosphite.

Very particularly preferred inorganic phosphoric acids and/or salts thereof are hypophosphorous acid and the sodium salt thereof.

Suitable organic 2-hydroxy acids and/or salts thereof are 2-hydroxy-2-sulfonatoacetic acid, 2-hydroxy-2-sulfonatopropionic acid, 2-hydroxy-2-phosphonatoacetic acid, 2-hydroxy-2-phosphonatopropionic acid, hydroxyethylidene-1,1'-diphosphonic acid, and the ammonium, sodium and potassium salts thereof.

Very particularly preferred organic 2-hydroxy acids and/or salts thereof are 2-hydroxy-2-sulfonatoacetic acid, 2-hydroxy-2-phosphonatoacetic acid and hydroxyethylidene-1,1'-diphosphonic acid, and the sodium salts thereof.

The presence of relatively large amounts of reducing agent, for example 2-hydroxy-2-sulfonatoacetic acid and salts thereof, in step i) has an adverse effect on the properties of the water-absorbing polymer particles, especially on the centrifuged retention capacity (CRC) and the extractables. Therefore, in step i), preferably less than 0.1% by weight, more preferably less than 0.02% by weight and most preferably less than 0.01% by weight of a reducing agent is used, based on the water-absorbing polymer particles. Reducing agents in the context of the present invention are compounds having heteroatoms which do not have the maximum oxidation number thereof. Sulfonic acids and phosphonic acids are thus not reducing agents in the context of the present invention.

Preference is given to adding the inorganic phosphoric acid and/or salt thereof after step i) and before step iii), and/or the organic 2-hydroxy acid and/or salt thereof before step i).

The inorganic phosphoric acid and/or salts thereof are reducing agents and are therefore preferably added only after polymerization has ended. When the inorganic phosphoric acids and/or salts thereof are added as an aqueous solution before drying, the solvent used can be removed in the course of drying without an additional step.

The organic 2-hydroxy acid and/or salts thereof are incorporated ideally into the water-absorbing polymer particles when they are added in a very early process step.

The use amount of inorganic phosphoric acid and/or salt thereof, based on the water-absorbing polymer particles, is preferably from 0.001 to 5% by weight, more preferably from 0.01 to 2% by weight, most preferably from 0.1 to 1% by weight.

The use amount of organic 2-hydroxy acid and/or salt thereof, based on the water-absorbing polymer particles, is preferably from 0.001 to 5% by weight, more preferably from 0.01 to 1.5% by weight, most preferably from 0.05 to 0.75% by weight.

The present invention is based on the finding that the inorganic phosphoric acids and organic 2-hydroxy acids for use in accordance with the invention act synergistically.

The production of the water-absorbing polymer particles is explained in detail hereinafter:

The water-absorbing polymer particles are produced by polymerizing a monomer solution or suspension and are typically water-insoluble.

The monomers a) are preferably water-soluble, i.e. the solubility in water at 23° C. is typically at least 1 g/100 g of water, preferably at least 5 g/100 g of water, more preferably at least 25 g/100 g of water, most preferably at least 35 g/100 g of water.

Suitable monomers a) are, for example, ethylenically unsaturated carboxylic acids, such as acrylic acid, methacrylic acid and itaconic acid. Particularly preferred monomers are acrylic acid and methacrylic acid. Very particular preference is given to acrylic acid.

Further suitable monomers a) are, for example, ethylenically unsaturated sulfonic acids, such as styrenesulfonic acid and 2-acrylamido-2-methylpropanesulfonic acid (AMPS).

Impurities can have a considerable influence on the polymerization. The raw materials used should therefore have a maximum purity. It is therefore often advantageous to specially purify the monomers a). Suitable purification processes are described, for example, in WO 2002/055469 A1, WO 2003/078378 A1 and WO 2004/035514 A1. A suitable monomer a) is, for example, acrylic acid purified according to WO 2004/035514 A1 comprising 99.8460% by weight of acrylic acid, 0.0950% by weight of acetic acid, 0.0332% by weight of water, 0.0203% by weight of propionic acid, 0.0001% by weight of furfurals, 0.0001% by weight of maleic anhydride, 0.0003% by weight of diacrylic acid and 0.0050% by weight of hydroquinone monomethyl ether.

The proportion of acrylic acid and/or salts thereof in the total amount of monomers a) is preferably at least 50 mol %, more preferably at least 90 mol %, most preferably at least 95 mol %.

The monomers a) typically comprise polymerization inhibitors, preferably hydroquinone monoethers, as storage stabilizers.

The monomer solution comprises preferably up to 250 ppm by weight, preferably at most 130 ppm by weight, more preferably at most 70 ppm by weight, preferably at least 10 ppm by weight, more preferably at least 30 ppm by weight, especially around 50 ppm by weight, of hydroquinone monoether, based in each case on the unneutralized monomer a). For example, the monomer solution can be prepared by using an ethylenically unsaturated monomer bearing acid groups with an appropriate content of hydroquinone monoether.

Preferred hydroquinone monoethers are hydroquinone monomethyl ether (MEHQ) and/or alpha-tocopherol (vitamin E).

Suitable crosslinkers b) are compounds having at least two groups suitable for crosslinking. Such groups are, for example, ethylenically unsaturated groups which can be polymerized free-radically into the polymer chain, and functional groups which can form covalent bonds with the acid groups of the monomer a). In addition, polyvalent metal salts which can form coordinate bonds with at least two acid groups of the monomer a) are also suitable as crosslinkers b).

Crosslinkers b) are preferably compounds having at least two polymerizable groups which can be polymerized free-radically into the polymer network. Suitable crosslinkers b) are, for example, ethylene glycol dimethacrylate, diethylene glycol diacrylate, polyethylene glycol diacrylate, allyl methacrylate, trimethylolpropane triacrylate, triallylamine, tetraallylammonium chloride, tetraallyloxyethane, as described in EP 0 530 438 A1, di- and triacrylates, as described in EP 0 547 847 A1, EP 0 559 476 A1, EP 0 632 068 A1, WO 93/21237 A1, WO 2003/104299 A1, WO 2003/104300 A1, WO 2003/104301 A1 and DE 103 31 450 A1, mixed acrylates which, as well as acrylate groups, comprise further ethylenically unsaturated groups, as described in DE 103 31 456 A1 and DE 103 55 401 A1, or crosslinker mixtures, as described, for example, in DE 195 43 368 A1, DE 196 46 484 A1, WO 90/15830 A1 and WO 2002/032962 A2.

Preferred crosslinkers b) are pentaerythrityl triallyl ether, tetraalloxyethane, methylenebismethacrylamide, 15-tuply ethoxylated trimethylolpropane triacrylate, polyethylene glycol diacrylate, trimethylolpropane triacrylate and triallylamine.

Very particularly preferred crosslinkers b) are the polyethoxylated and/or -propoxylated glycerols which have been esterified with acrylic acid or methacrylic acid to give di- or triacrylates, as described, for example, in WO 2003/104301 A1. Di- and/or triacrylates of 3- to 10-tuply ethoxylated glycerol are particularly advantageous. Very particular preference is given to di- or triacrylates of 1- to 5-tuply ethoxylated and/or propoxylated glycerol. Most preferred are the triacrylates of 3- to 5-tuply ethoxylated and/or propoxylated glycerol, especially the triacrylate of 3-tuply ethoxylated glycerol.

The amount of crosslinker b) is preferably 0.05 to 1.5% by weight, more preferably 0.1 to 1% by weight, most preferably 0.3 to 0.6% by weight, based in each case on monomer a). With rising crosslinker content, the centrifuge retention capacity (CRC) falls and the absorption under a pressure of 21.0 g/cm$^2$ passes through a maximum.

The initiators c) used may be all compounds which generate free radicals under the polymerization conditions, for example thermal initiators, redox initiators, photoinitiators.

Suitable redox initiators are sodium peroxodisulfate/ascorbic acid, hydrogen peroxide/ascorbic acid, sodium peroxodisulfate/sodium bisulfite and hydrogen peroxide/sodium bisulfite. Preference is given to using mixtures of thermal initiators and redox initiators, such as sodium peroxodisulfate/hydrogen peroxide/ascorbic acid. The reducing component used is, however, preferably the disodium salt of 2-hydroxy-2-sulfonatoacetic acid or a mixture of the disodium salt of 2-hydroxy-2-sulfinatoacetic acid, the disodium salt of 2-hydroxy-2-sulfonatoacetic acid and sodium bisulfite. Such mixtures are obtainable as Brüggolite® FF6 and Brüggolite® FF7 (Brüggemann Chemicals; Heilbronn; Germany).

Suitable photoinitiators are, for example, α-splitters, H-abstracting systems and azides. Suitable α-splitters or H-abstracting systems are, for example, benzophenone derivatives such as Michler's ketone, phenanthrene derivatives, fluorene derivatives, anthraquinone derivatives, thioxanthone derivatives, coumarin derivatives, benzoin ethers and derivatives thereof, azo initiators such as the abovementioned free-radical formers, substituted hexaaryl-bisimidazoles or acylphosphine oxides. Suitable azides are, for example, 2-(N,N-dimethylamino)ethyl 4-azidocinnamate, 2-(N,N-dimethylamino)ethyl 4-azidonaphthyl ketone, 2-(N,N-dimethylamino)ethyl 4-azidobenzoate, 5-azido-1-naphthyl 2'-(N,N-dimethylamino)ethyl sulfone, N-(4-sulfonylazidophenyl)maleimide, N-acetyl-4-sulfonylazidoaniline, 4-sulfonylazidoaniline, 4-azidoaniline, 4-azidophenacyl bromide, p-azidobenzoic acid, 2,6-bis(p-azidobenzylidene)cyclohexanone and 2,6-bis(p-azidobenzylidene)-4-methylcyclohexanone.

Ethylenically unsaturated monomers d) copolymerizable with the ethylenically unsaturated monomers a) bearing acid groups are, for example, acrylamide, methacrylamide, hydroxyethyl acrylate, hydroxyethyl methacrylate, dimethylaminoethyl methacrylate, dimethylaminoethyl acrylate, dimethylaminopropyl acrylate, diethylaminopropyl acrylate, dimethylaminoethyl methacrylate, diethylaminoethyl methacrylate.

The water-soluble polymers e) used may be polyvinyl alcohol, polyvinylpyrrolidone, starch, starch derivatives, modified cellulose, such as methylcellulose or hydroxyethylcellulose, gelatin, polyglycols or polyacrylic acids, preferably starch, starch derivatives and modified cellulose.

Typically, an aqueous monomer solution is used. The water content of the monomer solution is preferably from 40 to 75% by weight, more preferably from 45 to 70% by weight, most preferably from 50 to 65% by weight. It is also possible to use monomer suspensions, i.e. monomer solutions with excess monomer a), for example sodium acrylate. With rising water content, the energy requirement in the subsequent drying rises, and, with falling water content, the heat of polymerization can only be removed inadequately.

For optimal action, the preferred polymerization inhibitors require dissolved oxygen. The monomer solution can therefore be freed of dissolved oxygen before the polymerization by inertization, i.e. flowing an inert gas through, preferably nitrogen or carbon dioxide. The oxygen content of the monomer solution is preferably lowered before the polymerization to less than 1 ppm by weight, more preferably to less than 0.5 ppm by weight, most preferably to less than 0.1 ppm by weight.

In process step i), the monomer solution or suspension is polymerized. Suitable reactors are, for example, kneading reactors or belt reactors. In the kneader, the polymer gel formed in the polymerization of an aqueous monomer solution or suspension is comminuted continuously by, for example, contrarotatory stirrer shafts, as described in WO 2001/038402 A1. Polymerization on a belt is described, for example, in DE 38 25 366 A1 and U.S. Pat. No. 6,241,928. Polymerization in a belt reactor forms a polymer gel, which has to be comminuted in a further process step ii), for example in an extruder or kneader.

To improve the drying properties, the comminuted polymer gel obtained by means of a kneader can additionally be extruded.

However, it is also possible to dropletize an aqueous monomer solution and to polymerize the droplets obtained in a heated carrier gas stream. This allows the process steps of polymerization i) and drying ii) to be combined, as described in WO 2008/040715 A2 and WO 2008/052971 A1.

The acid groups of the resulting polymer gels have typically been partially neutralized. Neutralization is preferably carried out at the monomer stage. This is typically done by mixing in the neutralizing agent as an aqueous solution or preferably also as a solid. The degree of neutralization is preferably from 25 to 95 mol %, more preferably from 30 to 80 mol %, most preferably from 40 to 75 mol %, for which the customary neutralizing agents can be used, preferably alkali metal hydroxides, alkali metal oxides, alkali metal carbonates or alkali metal hydrogencarbonates and also mixtures thereof. Instead of alkali metal salts, it is also possible to use ammonium salts. Particularly preferred alkali metals are sodium and potassium, but very particular preference is given to sodium hydroxide, sodium carbonate or sodium hydrogencarbonate and also mixtures thereof.

However, it is also possible to carry out neutralization after the polymerization, at the stage of the polymer gel formed in the polymerization. It is also possible to neutralize up to 40 mol %, preferably 10 to 30 mol % and more preferably 15 to 25 mol % of the acid groups before the polymerization by adding a portion of the neutralizing agent actually to the monomer solution and setting the desired final degree of neutralization only after the polymerization, at the polymer gel stage. When the polymer gel is neutralized at least partly after the polymerization, the polymer gel is preferably comminuted mechanically, for example by means of an extruder, in which case the neutralizing agent can be sprayed, sprinkled or poured on and then carefully mixed in. To this end, the gel mass obtained can be repeatedly extruded for homogenization.

In process step iii), the resulting polymer gel is dried. The driers are not subject to any restriction. The drying of the polymer gel is, however, preferably carried out with a belt drier until the residual moisture content is preferably 0.5 to 15% by weight, more preferably 1 to 10% by weight, most preferably 2 to 8% by weight, the residual moisture content being determined by EDANA recommended test method No. WSP 230.2-05 "Moisture Content". In the case of too high a residual moisture content, the dried polymer gel has too low a glass transition temperature $T_g$ and can be processed further only with difficulty. In the case of too low a residual moisture content, the dried polymer gel is too brittle and, in the subsequent comminution steps, undesirably large amounts of polymer particles with an excessively low particle size ("fines") are obtained. The solids content of the gel before the drying is preferably from 25 to 90% by weight, more preferably from 35 to 70% by weight, most preferably from 40 to 60% by weight. Optionally, it is, however, also possible to use a fluidized bed drier or a paddle drier for the drying operation.

In process step iv), the dried polymer gel is ground and classified, and the apparatus used for grinding may typically be single- or multistage roll mills, preferably two- or three-stage roll mills, pin mills, hammer mills or vibratory mills.

The mean particle size of the polymer particles removed as the product fraction is preferably at least 200 µm, more preferably from 250 to 600 µm, very particularly from 300 to 500 µm. The mean particle size of the product fraction may be determined by means of EDANA recommended test method No. WSP 220.2-05 "Particle Size Distribution", where the proportions by mass of the screen fractions are plotted in cumulative form and the mean particle size is determined graphically. The mean particle size here is the value of the mesh size which gives rise to a cumulative 50% by weight.

The proportion of particles with a particle size of at least 150 µm is preferably at least 90% by weight, more preferably at least 95% by weight, most preferably at least 98% by weight.

Polymer particles with too small a particle size lower the permeability (SFC). The proportion of excessively small polymer particles ("fines") should therefore be small.

Excessively small polymer particles are therefore typically removed and recycled into the process. This is preferably done before, during or immediately after the polymerization, i.e. before the drying of the polymer gel. The excessively small polymer particles can be moistened with water and/or aqueous surfactant before or during the recycling.

It is also possible in later process steps to remove excessively small polymer particles, for example after the surface postcrosslinking or another coating step. In this case, the excessively small polymer particles recycled are surface postcrosslinked or coated in another way, for example with fumed silica.

When a kneading reactor is used for polymerization, the excessively small polymer particles are preferably added during the last third of the polymerization.

When the excessively small polymer particles are added at a very early stage, for example actually to the monomer solution, this lowers the centrifuge retention capacity (CRC) of the resulting water-absorbing polymer particles. However, this can be compensated, for example, by adjusting the amount of crosslinker b) used.

When the excessively small polymer particles are added at a very late stage, for example not until an apparatus connected downstream of the polymerization reactor, for example to an extruder, the excessively small polymer particles can be incorporated into the resulting polymer gel only with difficulty. Insufficiently incorporated, excessively small polymer particles are, however, detached again from the dried polymer gel during the grinding, are therefore removed again in the course of classification and increase the amount of excessively small polymer particles to be recycled.

The proportion of particles having a particle size of at most 850 µm is preferably at least 90% by weight, more preferably at least 95% by weight, most preferably at least 98% by weight.

The proportion of particles having a particle size of at most 600 µm is preferably at least 90% by weight, more preferably at least 95% by weight, most preferably at least 98% by weight.

Polymer particles with too great a particle size lower the swell rate. The proportion of excessively large polymer particles should therefore likewise be small.

Excessively large polymer particles are therefore typically removed and recycled into the grinding of the dried polymer gel.

To improve the properties, the polymer particles can be thermally surface postcrosslinked in a further process step v). Suitable surface postcrosslinkers are compounds which comprise groups which can form covalent bonds with at least two carboxylate groups of the polymer particles. Suitable compounds are, for example, polyfunctional amines, polyfunctional amidoamines, polyfunctional epoxides, as described in EP 0 083 022 A2, EP 0 543 303 A1 and EP 0 937 736 A2, di- or polyfunctional alcohols, as described in DE 33 14 019 A1, DE 35 23 617 A1 and EP 0 450 922 A2, or β-hydroxyalkylamides, as described in DE 102 04 938 A1 and U.S. Pat. No. 6,239,230.

Additionally described as suitable surface postcrosslinkers are cyclic carbonates in DE 40 20 780 C1, 2-oxazolidone and its derivatives, such as 2-hydroxyethyl-2-oxazolidone in DE 198 07 502 A1, bis- and poly-2-oxazolidinones in DE 198 07 992 C1, 2-oxotetrahydro-1,3-oxazine and its derivatives in DE 198 54 573 A1, N-acyl-2-oxazolidones in DE 198 54 574 A1, cyclic ureas in DE 102 04 937 A1, bicyclic amide acetals in DE 103 34 584 A1, oxetanes and cyclic ureas in EP 1 199 327 A2 and morpholine-2,3-dione and its derivatives in WO 2003/031482 A1.

Preferred surface postcrosslinkers are ethylene carbonate, ethylene glycol diglycidyl ether, reaction products of polyamides with epichlorohydrin, and mixtures of propylene glycol and 1,4-butanediol.

Very particularly preferred surface postcrosslinkers are 2-hydroxyethyloxazolidin-2-one, oxazolidin-2-one and 1,3-propanediol.

In addition, it is also possible to use surface postcrosslinkers which comprise additional polymerizable ethylenically unsaturated groups, as described in DE 37 13 601 A1.

The amount of surface postcrosslinkers is preferably 0.001 to 2% by weight, more preferably 0.02 to 1% by weight, most preferably 0.05 to 0.2% by weight, based in each case on the polymer particles.

In a preferred embodiment of the present invention, polyvalent cations are applied to the particle surface in addition to the surface postcrosslinkers before, during or after the surface postcrosslinking.

The polyvalent cations usable in the process according to the invention are, for example, divalent cations such as the cations of zinc, magnesium, calcium, iron and strontium, trivalent cations such as the cations of aluminum, iron, chromium, rare earths and manganese, tetravalent cations such as the cations of titanium and zirconium. Possible counterions are chloride, bromide, sulfate, hydrogensulfate, carbonate, hydrogencarbonate, nitrate, phosphate, hydrogenphosphate, dihydrogenphosphate and carboxylate, such as acetate and lactate. Aluminum sulfate and aluminum lactate are preferred. Apart from metal salts, it is also possible to use polyamines as polyvalent cations.

The amount of polyvalent cation used is, for example, 0.001 to 1.5% by weight, preferably 0.005 to 1% by weight, more preferably 0.02 to 0.8% by weight, based in each case on the polymer particles.

The surface postcrosslinking is typically performed in such a way that a solution of the surface postcrosslinker is sprayed onto the dried polymer particles. After the spraying, the polymer particles coated with surface postcrosslinker are dried thermally, and the surface postcrosslinking reaction can take place either before or during the drying.

The spray application of a solution of the surface postcrosslinker is preferably performed in mixers with moving mixing tools, such as screw mixers, disk mixers and paddle mixers. Particular preference is given to horizontal mixers such as paddle mixers, very particular preference to vertical mixers. The distinction between horizontal mixers and vertical mixers is made by the position of the mixing shaft, i.e. horizontal mixers have a horizontally mounted mixing shaft and vertical mixers a vertically mounted mixing shaft. Suitable mixers are, for example, horizontal Pflugschar® mixers (Gebr. Lödige Maschinenbau GmbH; Paderborn; Germany), Vrieco-Nauta continuous mixers (Hosokawa Micron BV; Doetinchem; the Netherlands), Processall Mixmill mixers (Processall Incorporated; Cincinnati; US) and Schugi Flexomix® (Hosokawa Micron BV; Doetinchem; the Netherlands). However, it is also possible to spray on the surface postcrosslinker solution in a fluidized bed.

The surface postcrosslinkers are typically used in the form of an aqueous solution. The content of nonaqueous solvent and/or total amount of solvent can be used to adjust the penetration depth of the surface postcrosslinker into the polymer particles.

When exclusively water is used as the solvent, a surfactant is advantageously added. This improves the wetting performance and reduces the tendency to form lumps. However, preference is given to using solvent mixtures, for example isopropanol/water, 1,3-propanediol/water and propylene glycol/water, where the mixing ratio by mass is preferably from 20:80 to 40:60.

The thermal surface postcrosslinking is preferably carried out in contact driers, more preferably paddle driers, most preferably disk driers. Suitable driers are, for example, Hosokawa Bepex® horizontal paddle driers (Hosokawa Micron GmbH; Leingarten; Germany), Hosokawa Bepex® disk driers (Hosokawa Micron GmbH; Leingarten; Germany) and Nara paddle driers (NARA Machinery Europe; Frechen; Germany). Moreover, it is also possible to use fluidized bed driers.

The thermal surface postcrosslinking can be effected in the mixer itself, by heating the jacket or blowing in warm air. Equally suitable is a downstream drier, for example a shelf drier, a rotary tube oven or a heatable screw. It is particularly advantageous to mix and dry in a fluidized bed drier.

Preferred surface postcrosslinking temperatures are in the range of 100 to 250° C., preferably 120 to 220° C., more preferably 130 to 210° C., most preferably 150 to 200° C. The preferred residence time at this temperature in the reaction mixer or drier is preferably at least 10 minutes, more preferably at least 20 minutes, most preferably at least 30 minutes, and typically at most 60 minutes.

Subsequently, the surface postcrosslinked polymer particles can be classified again, excessively small and/or excessively large polymer particles being removed and recycled into the process.

To further improve the properties, the surface postcrosslinked polymer particles can be coated or remoisturized.

The remoisturizing is carried out preferably at 30 to 80° C., more preferably at 35 to 70° C. and most preferably at 40 to 60° C. At excessively low temperatures, the water-absorbing polymer particles tend to form lumps, and, at higher temperatures, water already evaporates noticeably. The amount of water used for remoisturizing is preferably from 1 to 10% by weight, more preferably from 2 to 8% by weight and most preferably from 3 to 5% by weight. The remoisturizing increases the mechanical stability of the polymer particles and reduces their tendency to static charging.

Suitable coatings for improving the swell rate and the permeability (SFC) are, for example, inorganic inert substances, such as water-insoluble metal salts, organic polymers, cationic polymers and di- or polyvalent metal cations. Suitable coatings for dust binding are, for example, polyols. Suitable coatings for counteracting the undesired caking tendency of the polymer particles are, for example, fumed silica, such as Aerosil® 200, and surfactants, such as Span® 20.

The present invention further provides the water-absorbing polymer particles obtainable by the process according to the invention.

The present invention further provides water-absorbing polymer particles comprising a') at least one polymerized ethylenically unsaturated monomer a) which bears acid groups and may be at least partly neutralized, b') at least one polymerized crosslinker b), c') optionally one or more ethylenically unsaturated monomers d) copolymerized with the monomers mentioned under a) and d') optionally one or more water-soluble polymers e), said water-absorbing polymer particles comprising at least one inorganic phosphoric acid and/or salt thereof and at least one organic 2-hydroxy acid and/or salt thereof, where the phosphorus in the inorganic phosphoric acid has an oxidation number of less than +V and the organic 2-hydroxy acid does not have a polymeric structure. Organic 2-hydroxy acids with polymeric structure form when 2-hydroxy acids with ethylenically unsaturated groups are used in the polymerization.

The water-absorbing polymer particles produced by the process according to the invention have a centrifuge retention capacity (CRC) of typically at least 15 g/g, preferably at least 20 g/g, preferentially at least 22 g/g, more preferably at least 24 g/g, most preferably at least 26 g/g. The centrifuge retention capacity (CRC) of the water-absorbing polymer particles is typically less than 60 g/g. The centrifuge retention capacity (CRC) is determined by EDANA recommended test method No. WSP 241.2-05 "Centrifuge Retention Capacity".

The water-absorbing polymer particles produced by the process according to the invention have an absorption under a pressure of 49.2 g/cm$^2$ of typically at least 15 g/g, preferably at least 20 g/g, preferentially at least 22 g/g, more preferably at least 24 g/g, most preferably at least 26 g/g. The absorption under a pressure of 49.2 g/cm$^2$ of the water-absorbing polymer particles is typically less than 35 g/g. The absorption under a pressure of 49.2 g/cm$^2$ is determined analogously to EDANA recommended test method No. WSP 242.2-05 "Absorption under Pressure", except that a pressure of 49.2 g/cm$^2$ is established instead of a pressure of 21.0 g/cm$^2$.

The present invention further provides hygiene articles comprising at least one inventive composition, especially hygiene articles for feminine hygiene, hygiene articles for light and heavy incontinence, or small animal litter.

The hygiene articles typically comprise a water-impervious backside, a water-pervious topside and, in between, an absorbent core composed of the inventive water-absorbing polymer particles and fibers, preferably cellulose. The proportion of the inventive water-absorbing polymer particles in the absorbent core is preferably 20 to 100% by weight, more preferably 50 to 100% by weight.

The water-absorbing polymer particles are tested by means of the test methods described hereinafter.

The standard test methods designated "WSP" are described in: "Standard Test Methods for the Nonwovens Industry", 2005 edition, jointly published by the "Worldwide Strategic Partners" EDANA (Avenue Eugène Plasky 157, 1030 Brussels, Belgium, www.edana.org) and INDA (1100 Crescent Green, Cary, N.C. 27518, U.S.A., www.inda.org). This publication is obtainable both from EDANA and from INDA.

Methods

The measurements should, unless stated otherwise, be carried out at an ambient temperature of 23±2° C. and a relative air humidity of 50±10%. The water-absorbing polymer particles are mixed thoroughly before the measurement.

Centrifuge Retention Capacity

The centrifuge retention capacity (CRC) is determined by EDANA recommended test method No. WSP 241.2-05 "Centrifuge Retention Capacity".

Absorption Under a Pressure of 49.2 g/cm$^2$

The absorption under a pressure of 49.2 g/cm$^2$ (AUL0.7 psi) is determined analogously by EDANA recommended test method No. WSP 242.2-05 "Absorption under Pressure", except that a pressure of 49.2 g/(AUL0.7 psi) is established instead of a pressure of 21.0 g/cm$^2$ (AUL0.3 psi).

Extractables

Extractables are determined by EDANA recommended test method No. WSP 270.2-05 "Extractable".

Saline Flow Conductivity

The saline flow conductivity (SFC) of a swollen gel layer under a pressure of 0.3 psi (2070 Pa) is determined, as described in EP 0 640 330 A1, as the gel layer permeability of a swollen gel layer of water-absorbing polymer particles, the apparatus described in the aforementioned patent application on page 19 and in FIG. 8 having been modified to the effect that the glass frit (40) is not used, the plunger (39) consists of the same polymer material as the cylinder (37) and now comprises 21 bores of equal size distributed homogeneously over the entire contact area. The procedure and evaluation of the measurement remain unchanged from EP 0 640 330 A1. The flow is detected automatically.

The saline flow conductivity (SFC) is calculated as follows:

$$\text{SFC }[\text{cm}^3\text{s/g}]=(Fg(t=0)\times L0)/(d\times A\times WP)$$

where Fg(t=0) is the flow of NaCl solution in g/s, which is obtained with reference to a linear regression analysis of the Fg(t) data of the flow determinations by extrapolation to t=0, L0 is the thickness of the gel layer in cm, d is the density of the NaCl solution in g/cm$^3$, A is the area of the gel layer in cm$^2$ and WP is the hydrostatic pressure over the gel layer in dyn/cm$^2$.

Gel Bed Permeability

The gel bed permeability (GBP) of a swollen gel layer under a pressure of 0.3 psi (2070 Pa) is determined, as described in US 2005/02567575 (paragraphs [0061] and [0075]), as the gel bed permeability of a swollen gel layer of water-absorbing polymer particles.

CIE Color Number (L, a, b)

The color analysis is carried out according to the CIELAB method (Hunterlab, Volume 8, 1996, Book 7, pages 1 to 4) with a "LabScan XE S/N LX17309" colorimeter (HunterLab, Reston, US). This method describes the colors via the coordinates L, a and b of a three-dimensional system. L indicates the brightness, where L=0 means black and L=100 white. The values of a and b indicate the positions of the color on the red/green and yellow/blue color axes respectively, where +a represents red, −a represents green, +b represents yellow and −b represents blue. The HC60 value is calculated by the formula HC60=L−3b.

The color measurement corresponds to the three-area method according to DIN 5033-6.

Aging Test

Measurement 1 (initial color): A plastic dish of internal diameter 9 cm is overfilled with superabsorbent particles which are then smoothed flat with a blade over the edge, and the CIE color numbers and the HC60 value are determined.

Measurement 2 (after aging): A plastic dish of internal diameter 9 cm is overfilled with superabsorbent particles which are then smoothed flat with a blade over the edge. The dish is then placed open into a climate-controlled cabinet heated to 60° C. with constant relative air humidity of 86%. After 21 days have passed, the dish is taken out. After cooling to room temperature, the CIE color numbers and the HC60 value are determined again.

EXAMPLES

Example 1

Comparative Example

A 2 l stainless steel beaker was initially charged with 326.7 g of 50% by weight sodium hydroxide solution and 849 g of frozen demineralized water. 392.0 g of acrylic acid were added while stirring, in the course of which the rate of addition was adjusted such that the temperature did not exceed 35° C. The mixture was then cooled with the aid of a cooling bath while stirring. Once the temperature of the mixture had fallen to 20° C., 0.804 g of triply ethoxylated glycerol triacrylate, 0.041 g of 2-hydroxy-2-methyl-1-phenylpropan-1-one (DAROCUR®1173; Ciba Specialty Chemicals Inc.; Basle; Switzerland) and 0.014 g of 2,2-dimethoxy-1,2-diphenylethan-1-one (IRGACURE® 651; Ciba Specialty Chemicals Inc.; Basle; Switzerland) were added. Cooling was continued and, on attainment of 15° C., the mixture was freed of oxygen by passing nitrogen through by means of a glass frit. On attainment of 0° C., 0.482 g of sodium persulfate (dissolved in 5 ml of demineralized water) and 0.197 g of 30% by weight hydrogen peroxide solution (dissolved in 6 ml of demineralized water) were added, and the monomer solution was transferred to a glass dish. The dimensions of the glass dish were such that a layer thickness of the monomer solution of 5 cm was established. Subsequently, 0.020 g of ascorbic acid (dissolved in 5 ml of demineralized water) was added and the monomer solution was stirred briefly with the aid of a glass rod. The glass dish containing the monomer solution was placed under a UV lamp (UV intensity=20 mW/cm$^2$), in the course of which polymerization set in. After 16 minutes, the resulting polymer gel was extruded three times with the aid of a commercial meat grinder with a 6 mm perforated plate, and dried in a forced air drying cabinet at 160° C. for one hour. The dried polymer gel was then ground and screened off to a particle size of 150 to 600 µm.

For surface postcrosslinking, this base polymer was coated in a Pflugschar® M5 mixer with a heating jacket (Gebr. Lödige Maschinenbau GmbH; Paderborn; Germany) at 23° C. and a shaft speed of 450 revolutions per minute, by means of a two-substance spray nozzle, with a mixture of 1.0% by weight of 1,3-propanediol, 0.06% by weight of N-(2-hydroxyethyl)-2-oxazolidinone, 2.3% by weight of demineralized water and 0.3% by weight of aqueous aluminum lactate solution (22% strength by weight), based in each case on the base polymer.

After the spray application, the product temperature was increased to 170° C. and the reaction mixture was kept at this temperature and at a shaft speed of 60 revolutions per minute for 60 minutes. The resulting product was allowed to cool again to ambient temperature. The surface postcrosslinked water-absorbing polymer particles were screened off to a particle size of 150 µm to 600 µm and had the following properties:
CRC=37.4 g/g
AUL0.7 psi=16.4 g/g
Extractables=12.8% by weight
The resulting water-absorbing polymer particles had a CIE color number of L=88.7, a=−0.6 and b=9.1, and a HC60 value of 61.4.

Example 2

Comparative Example

The procedure was as in example 1. 0.392 g of the disodium salt of 2-hydroxy-2-sulfonatoacetic acid (dissolved in 10 ml of demineralized water) was added to the monomer solution instead of the 0.020 g of ascorbic acid.
The surface postcrosslinked water-absorbing polymer particles were screened off to a particle size of 150 µm to 600 µm and had the following properties:
CRC=37.7 g/g
AUL0.7 psi=17.1 g/g
Extractables=13.4% by weight
The resulting water-absorbing polymer particles had a CIE color number of L=90.0, a=−0.8 and b=8.5, and an HC60 value of 64.5.

Example 3

Comparative Example

The procedure was as in example 1. 0.980 g of the disodium salt of 2-hydroxy-2-sulfonatoacetic acid (dissolved in 15 ml of demineralized water) was added to the monomer solution instead of the 0.020 g of ascorbic acid.
The surface postcrosslinked water-absorbing polymer particles were screened off to a particle size of 150 µm to 600 µm and had the following properties:
CRC=37.9 g/g
AUL0.7 psi=16.8 g/g
Extractables=13.9% by weight
The resulting water-absorbing polymer particles had a CIE color number of L=90.3, a=−0.8 and b=7.9, and an HC60 value of 66.6.

Example 4

The procedure was as in example 1. 0.392 g of the disodium salt of 2-hydroxy-2-sulfonatoacetic acid (dissolved in 10 ml of demineralized water) was added to the monomer solution instead of the 0.020 g of ascorbic acid. In addition, the polymer gel which had been extruded three times was admixed with 1.96 g of sodium hypophosphite (dissolved in 10 ml of demineralized water) and extruded twice more.
The surface postcrosslinked water-absorbing polymer particles were screened off to a particle size of 150 µm to 600 µm and had the following properties:
CRC=37.5 g/g
AUL0.7 psi=16.6 g/g
Extractables=13.6% by weight
The resulting water-absorbing polymer particles had a CIE color number of L=90.5, a=−0.8 and b=6.9, and an HC60 value of 69.8.

Example 5

The procedure was as in example 1. 0.392 g of the disodium salt of 2-hydroxy-2-sulfonatoacetic acid (dissolved in 10 ml of demineralized water) was added to the monomer solution instead of the 0.020 g of ascorbic acid. In addition, the polymer gel which had been extruded three times was admixed with 3.92 g of sodium hypophosphite (dissolved in 15 ml of demineralized water) and extruded twice more.
The surface postcrosslinked water-absorbing polymer particles were screened off to a particle size of 150 µm to 600 µm and had the following properties:
CRC=37.8 g/g
AUL0.7 psi=16.9 g/g
Extractables=13.8% by weight
The resulting water-absorbing polymer particles had a CIE color number of L=91.1, a=−0.8 and b=6.3, and an HC60 value of 72.2.

Example 6

Comparative Example

The procedure was as in example 1. In addition, the polymer gel which had been extruded three times was admixed with 3.92 g of sodium hypophosphite (dissolved in 15 ml of demineralized water) and extruded twice more.
The surface postcrosslinked water-absorbing polymer particles were screened off to a particle size of 150 µm to 600 µm and had the following properties:
CRC=37.9 g/g
AUL0.7 psi=16.2 g/g
Extractables=13.5% by weight
The resulting water-absorbing polymer particles had a CIE color number of L=89.1, a=−0.7 and b=8.2, and an HC60 value of 74.5.

Example 7

The procedure was as in example 1. 0.392 g of Brüggolite® FF6 (dissolved in 10 ml of demineralized water) was added to the monomer solution instead of the 0.020 g of ascorbic acid. Brüggolite® FF6 is a mixture of the sodium salt of 2-hydroxy-2-sulfonatoacetic acid, the disodium salt of 2-hydroxy-2-sulfonatoacetic acid and sodium bisulfite (Brüggemann Chemicals; Heilbronn; Germany). In addition, the polymer gel which had been extruded three times was admixed with 1.96 g of sodium hypophosphite (dissolved in 10 ml of demineralized water) and extruded twice more.
The surface postcrosslinked water-absorbing polymer particles were screened off to a particle size of 150 µm to 600 µm and had the following properties:
CRC=43.9 g/g
AUL0.7 psi=11.7 g/g
Extractables=28.9% by weight
The resulting water-absorbing polymer particles had a CIE color number of L=90.1, a=−0.7 and b=7.4, and an HC60 value of 67.9.

Example 8

The procedure was as in example 1. 0.980 g of 2-hydroxy-2-phosphonatoacetic acid (dissolved in 15 ml of demineralized water) was added to the monomer solution instead of the 0.020 g of ascorbic acid. In addition, the polymer gel which had been extruded three times was admixed with 1.96 g of sodium hypophosphite (dissolved in 10 ml of demineralized water) and extruded twice more.

The surface postcrosslinked water-absorbing polymer particles were screened off to a particle size of 150 μm to 600 μm and had the following properties:
CRC=37.4 g/g
AUL0.7 psi=17.3 g/g
Extractables=12.8% by weight
The resulting water-absorbing polymer particles had a CIE color number of L=90.7, a=−0.8 and b=6.8, and an HC60 value of 70.3.

Example 9

The procedure was as in example 1. 1.57 g of 1-hydroxy-1,1'-ethylidenediphosphonic acid (dissolved in 20 ml of demineralized water) was added to the monomer solution instead of the 0.020 g of ascorbic acid. In addition, the polymer gel which had been extruded three times was admixed with 2.65 g of sodium hypophosphite (dissolved in 10 ml of demineralized water) and extruded twice more.
The surface postcrosslinked water-absorbing polymer particles were screened off to a particle size of 150 μm to 600 μm and had the following properties:
CRC=38.1 g/g
AUL0.7 psi=16.5 g/g
Extractables=14.0% by weight
The resulting water-absorbing polymer particles had a CIE color number of L=91.0, a=−0.9 and b=6.2, and an HC60 value of 72.4.

Example 10

The procedure was as in example 1. In addition, the polymer gel which had been extruded three times was admixed with 3.14 g of sodium hypophosphite (dissolved in 10 ml of demineralized water) and 1.18 g of 2-hydroxy-2-phosphonatoacetic acid (dissolved in 10 ml of demineralized water) and extruded twice more.
The surface postcrosslinked water-absorbing polymer particles were screened off to a particle size of 150 μm to 600 μm and had the following properties:
CRC=37.9 g/g
AUL0.7 psi=17.4 g/g
Extractables=13.0% by weight
The resulting water-absorbing polymer particles had a CIE color number of L=90.7, a=−0.7 and b=7.1, and an HC60 value of 69.4.

Example 11

The procedure was as in example 1. 0.980 g of sodium hypophosphite (dissolved in 5 ml of demineralized water) was added to the monomer solution instead of the 0.020 g of ascorbic acid. In addition, the polymer gel which had been extruded three times was admixed with 1.18 g of 2-hydroxy-2-phosphonatoacetic acid (dissolved in 10 ml of demineralized water) and extruded twice more.
The surface postcrosslinked water-absorbing polymer particles were screened off to a particle size of 150 μm to 600 μm and had the following properties:
CRC=57.3 g/g
AUL0.7 psi=10.2 g/g
Extractables=46.8% by weight
The resulting water-absorbing polymer particles had a CIE color number of L=89.6, a=−0.8 and b=8.0, and an HC60 value of 65.4.

Example 12

A Pflugschar® VT 5R-MK paddle drier of capacity 5 l (Gebr. Lödige Maschinenbau GmbH; Paderborn: Germany) was initially charged with 468 g of demineralized water, 244.3 g of acrylic acid, 1924.9 g of aqueous sodium acrylate solution (37.3% strength by weight) and 3.28 g of Sartomer® SR-344 (diacrylate of a polyethylene glycol having a molar mass of approx. 400 g/mol), and inertized by sparging with nitrogen for 20 minutes. The shaft of the reactor was constantly rotated at 96 revolutions per minute. The reaction mixture was cooled from the outside such that the subsequent addition of initiator was effected at approx. 20° C. Finally, 2.139 g of sodium persulfate (dissolved in 12.12 g of demineralized water), 1.19 g of the disodium salt of 2-hydroxy-2-sulfonatoacetic acid (dissolved in 20 ml of demineralized water) and 0.127 g of 30% by weight aqueous hydrogen peroxide solution (diluted with 1.15 g of demineralized water) were added in rapid succession to the Pflugschar® paddle drier while stirring. The reaction set in rapidly and, on attainment of an internal temperature of 30° C., the jacket was heated with heat carrier medium at 80° C. in order to conduct the reaction to the end under very substantially adiabatic conditions. On attainment of the maximum temperature, the mixture was cooled again (cooling liquid at −12° C.), such that the polymer gel formed was cooled to below 50° C. and then discharged. The resulting polymer gel was extruded three times with the aid of a commercial meat grinder with a 6 mm perforated plate, admixed with 3.97 g of sodium hypophosphite (dissolved in 15 ml of demineralized water) and extruded twice more. The polymer gel was then dried in a forced-air drying cabinet at 160° C. for one hour. The dried polymer gel was then ground and screened off to a particle size of 150 to 710 μm.
For surface postcrosslinking, this base polymer was coated in a Pflugschar® M5 mixer with a heating jacket (Gebr. Lödige Maschinenbau GmbH; Paderborn; Germany) at 23° C. and a shaft speed of 450 revolutions per minute, by means of a two-substance spray nozzle, with a mixture of 1.0% by weight of 1,2-propanediol, 0.125% by weight of N-(2-hydroxyethyl)-2-oxazolidinone, 1.5% by weight of demineralized water, 0.003% by weight of Span® 20 (sorbitan monolaurate) and 2.8% by weight of aqueous aluminum sulfate solution (26.8% strength by weight), based in each case on the base polymer.
After the spray application, the product temperature was increased to 180° C. and the reaction mixture was kept at this temperature and at a stirrer speed of 60 revolutions per minute for 50 minutes. The resulting product was allowed to cool again to ambient temperature. The surface postcrosslinked water-absorbing polymer particles were screened off to a particle size of 150 to 710 μm, and had the following properties:
CRC=27.5 g/g
AUL0.7 psi=22.6 g/g
SFC=145×10$^{-7}$ cm$^3$s/g
GBP=120 darcies.
The resulting water-absorbing polymer particles had a CIE color number of L=92.5, a=−0.5 and b=3.6, and an HC60 value of 81.7.

Example 13

The procedure was as in example 12. 0.020 g of ascorbic acid (dissolved in 10 ml of demineralized water) was added to the monomer solution instead of the disodium salt of 2-hydroxy-2-sulfonatoacetic acid. In addition, the polymer gel which had been extruded three times was admixed with 4.77 g of sodium hypophosphite (dissolved in 15 ml of demineralized water) and 4.77 g of the disodium salt of 1-hydroxy-1,1'-ethylidenediphosphonic acid (dissolved in 30 ml of demineralized water) instead of with 3.97 g of sodium hypophosphite, and extruded twice more.

The surface postcrosslinked water-absorbing polymer particles were screened off to a particle size of 150 μm to 710 μm and had the following properties:
CRC=28.1 g/g
AUL0.7 psi=23.8 g/g
SFC=138×10$^{-7}$ cm$^3$s/g
GBP=12 darcies.

The resulting water-absorbing polymer particles had a CIE color number of L=92.8, a=−0.8 and b=4.0, and an HC60 value of 80.8.

Example 14

14.3 kg of aqueous sodium acrylate solution (37.5% strength by weight), 1.4 kg of acrylic acid and 350 g of demineralized water were mixed with 10.6 g of triply ethoxylated glyceryl triacrylate. This solution was dropletized in a heated dropletizing tower filled with a nitrogen atmosphere (180° C., height 12 m, diameter 2 m, gas velocity 0.1 m/s in cocurrent, dropletizer of diameter 40 mm, internal height 2 mm, and a dropletizer plate with 60 bores each of diameter 200 μm) at a metering rate of 32 kg/h. The temperature of the solution was 25° C. Just upstream of the dropletizer, the monomer solution was mixed with three solutions by means of a static mixer. Solution 1 was a 6% by weight solution of 2,2'-azobis[2-(2-imidazolin-2-yl)propane]dihydrochloride in demineralized water, solution 2 was a 6% by weight solution of sodium peroxodisulfate in demineralized water, and solution 3 was a 10% by weight solution of 2-hydroxy-2-phosphonatoacetic acid in demineralized water. The metering rate of solution 1 was 0.642 kg/h, the metering rate of solution 2 was 0.458 kg/h, and the metering rate of solution 3 was 0.275 kg/h. The resulting polymer particles were screened off to a particle size of 150 to 850 μm, in order to remove any agglomerates formed.

This base polymer was coated in a Pflugschar® M5 mixer with a heating jacket (Gebr. Lödige Maschinenbau GmbH; Paderborn; Germany) at 23° C. and a shaft speed of 250 revolutions per minute, by means of a two-substance spray nozzle, with 2.0% by weight of a 30% by weight aqueous sodium hypophosphite solution, based on the base polymer.

After the spray application, the reaction mixture was kept at a shaft speed of 60 revolutions per minute for 15 minutes. The coated water-absorbing polymer particles were screened off to a particle size of 150 to 850 μm and had the following properties:
CRC=32.7 g/g
AUL0.7 psi=23.2 g/g
SFC=20×10$^{-7}$ cm$^3$s/g The resulting water-absorbing polymer particles had a CIE color number of L=93.4, a=0.3 and b=2.4, and an HC60 value of 86.2.

Example 15

The procedure was as in example 14. Solution 3 was a 7% by weight solution of the disodium salt of 2-hydroxy-2-sulfonatoacetic acid in demineralized water. The metering rate of solution 1 was altered to 0.275 kg/h, and the metering rate of solution 3 was 0.314 kg/h.

For surface postcrosslinking, the resulting base polymer was coated in a Pflugschar® M5 mixer with a heating jacket (Gebr. Lödige Maschinenbau GmbH; Paderborn; Germany) at 23° C. and a shaft speed of 450 revolutions per minute, by means of a two-substance spray nozzle, with a mixture of 1.0% by weight of 1,2-propanediol, 0.1% by weight of ethylene glycol diglycidyl ether, 1.0% by weight of demineralized water, and 2.0% by weight of aqueous sodium hypophosphite solution (30% strength by weight), based in each case on the base polymer.

After the spray application, the product temperature was increased to 150° C. and the reaction mixture was kept at this temperature and a shaft speed of 60 revolutions per minute for 60 minutes. The resulting product was allowed to cool again to ambient temperature. The surface postcrosslinked water-absorbing polymer particles were screened off to a particle size of 150 μm to 850 μm.

150 g of the surface postcrosslinked polymer particles were admixed in a 500 ml polyethylene bottle with 0.30 g of Sipernat® D17 (hydrophobic precipitated silica), and mixed intimately by means of a T2C tumbling mixer (Willy A. Bachofen AG Maschinenfabrik; Basle; Switzerland) for 15 minutes.

The coated water-absorbing polymer particles had the following properties:
CRC=28.2 g/g
AUL0.7 psi=22.0 g/g
SFC=31×10$^{-7}$ cm$^3$s/g The resulting water-absorbing polymer particles had a CIE color number of L=93.2, a=0.4 and b=2.5, and an HC60 value of 85.7.

TABLE 1

| Results after the aging test | | | | |
|---|---|---|---|---|
| Example | L | a | b | HC 60 |
| 1*) | 59.6 | 6.5 | 14.8 | 15.2 |
| 2*) | 80.2 | 1.1 | 13.6 | 39.4 |
| 3*) | 81.4 | 1.0 | 13.4 | 41.2 |
| 4 | 83.2 | 0.1 | 7.8 | 59.8 |
| 5 | 83.8 | −0.1 | 7.3 | 61.9 |
| 6*) | 77.3 | 4.9 | 12.1 | 41.0 |
| 7 | 82.8 | 0.4 | 9.0 | 55.8 |
| 8 | 83.6 | 0.3 | 7.7 | 60.5 |
| 9 | 84.2 | −0.2 | 7.0 | 63.2 |
| 10 | 83.0 | 0.4 | 8.1 | 58.7 |
| 11 | 82.5 | 0.7 | 8.5 | 57.0 |
| 12 | 84.6 | −0.3 | 6.9 | 63.9 |
| 13 | 83.9 | −0.1 | 7.4 | 61.7 |
| 14 | 85.1 | −0.4 | 6.3 | 66.2 |
| 15 | 85.2 | −0.5 | 6.1 | 66.9 |

*)Comparative examples

The invention claimed is:

1. A process for producing water-absorbing polymer particles by polymerizing a monomer solution or suspension comprising
   a) at least one ethylenically unsaturated monomer which bears an acid group and may be at least partly neutralized,
   b) at least one crosslinker,
   c) at least one initiator,
   d) optionally one or more ethylenically unsaturated monomer copolymerizable with the monomer mentioned under a) and
   e) optionally one or more water-soluble polymer, comprising polymerizing the monomer solution or suspension to give a polymer gel i), optionally comminuting the resulting polymer gel ii), drying the polymer gel iii), grinding and classifying the dried polymer gel to polymer particles iv), and optionally thermally surface postcrosslinking the classified polymer particles v), which comprises adding, at least one of hypophosphorous acid and phosphorous acid and salt thereof after step i) and before, during, or after one of step ii) to v), and at least one organic 2-hydroxy acid selected from the group consisting of 2-hydroxy-2-sulfonatoacetic acid, a 2-hydroxy-2-phosphonoacetic acid, and hydroxyethylidene-1,1'-diphosphonic acid and a salt thereof before step i), where the at least one of hypophosphorous acid and phosphorous acid and salt thereof is present in a vicinity of the water-absorbing particle surface.

2. The process according to claim 1, wherein the at least one of hypophosphorous acid and phosphorous acid and salt thereof is added after step i) and before step iii).

3. The process according to claim 1, wherein the at least one initiator c) comprises a peroxide, and is added in step i).

4. The process according to claim 1, wherein from 0.001 to 5% by weight of the at least one of hypophosphorous acid and phosphorous acid and salt thereof, based on the water-absorbing polymer particles, is added.

5. The process according to claim 1, wherein from 0.001 to 5% by weight of the organic 2-hydroxy acid and/or salt thereof, based on the water-absorbing polymer particles, is added.

6. The Water-absorbing polymer particles prepared by a process according to claim 1 wherein the organic 2-hydroxy acid is distributed throughout the water absorbing particle.

7. Water-absorbing polymer particles comprising
   a') at least one polymerized ethylenically unsaturated monomer which bears an acid group and may be at least partly neutralized,
   b') at least one polymerized crosslinker,
   c') optionally one or more ethylenically unsaturated monomer copolymerized with the monomer mentioned under a), and
   d') optionally one or more water-soluble polymer, said water-absorbing polymer particles comprising
      at least one of hypophosphorous acid and phosphorous acid and salt thereof, and
      at least one organic 2-hydroxy acid selected from the group consisting of 2-hydroxy-2-sulfonatoacetic acid, a 2-hydroxy-2-phosphonoacetic acid, and hydroxyethylidene-1,1'-diphosphonic acid and a salt thereof,
   wherein the organic 2-hydroxy acid is distributed throughout the water-absorbing particle and the at least one of hypophosphorous acid and phosphorous acid and salt thereof is present in the vicinity of the water-absorbing polymer particle surface.

8. The Water-absorbing polymer particles according to claim 7, wherein the polymer particles comprise from 0.001 to 5% by weight of the at least one of hypophosphorous acid and phosphorous acid and salt thereof.

9. The Water-absorbing polymer particles according to claim 7, wherein the polymer particles comprise from 0.001 to 5% by weight of the organic 2-hydroxy acid and/or salt thereof.

10. The Water-absorbing polymer particles according to claim 7, which have a centrifuge retention capacity of at least 15 g/g.

11. A hygiene article comprising water-absorbing polymer particles prepared by the process according to claim 1, or water-absorbing polymer particles according to claim 6.

12. The process according to claim 1, wherein the 2-hydroxy acid is 2-hydroxy-2-sulfonatoacetic acid.

\* \* \* \* \*